(12) United States Patent
Hsu et al.

(10) Patent No.: US 11,759,488 B2
(45) Date of Patent: Sep. 19, 2023

(54) USE OF ANTRODIA CINNAMOMEA FOR INCREASING ALCOHOL METABOLISM

(71) Applicant: Greenyn Biotechnology Co., Ltd, Taichung (TW)

(72) Inventors: Pang-Kuei Hsu, Taichung (TW); Chia-Feng Wu, Taichung (TW)

(73) Assignee: GREENYN BIOTECHNOLOGY CO., LTD, Taichung (TW)

(*) Notice: Subject to any disclaimer, the term of this patent is extended or adjusted under 35 U.S.C. 154(b) by 24 days.

(21) Appl. No.: 17/203,145

(22) Filed: Mar. 16, 2021

(65) Prior Publication Data

US 2021/0290709 A1    Sep. 23, 2021

(30) Foreign Application Priority Data

Mar. 18, 2020    (TW) ................. 109108997

(51) Int. Cl.
| | | |
|---|---|---|
| *A61K 36/00* | (2006.01) | |
| *A61K 36/07* | (2006.01) | |
| *A61P 25/32* | (2006.01) | |
| *A61K 9/00* | (2006.01) | |

(52) U.S. Cl.
CPC ............ *A61K 36/07* (2013.01); *A61K 9/0053* (2013.01); *A61P 25/32* (2018.01)

(58) Field of Classification Search
CPC .......................... A61P 25/32; A23V 2200/334
See application file for complete search history.

(56) References Cited

U.S. PATENT DOCUMENTS

| | | | |
|---|---|---|---|
| 2016/0257768 A1 | 9/2016 | Chuang et al. | |
| 2017/0281573 A1 | 10/2017 | Schwarz et al. | |

FOREIGN PATENT DOCUMENTS

| | | | |
|---|---|---|---|
| CN | 10389221 | * | 12/2012 |
| CN | 103893221 | | 7/2014 |
| CN | 104027364 | | 9/2014 |
| CN | 108243834 | * | 7/2018 |
| JP | 2016210770 | | 12/2016 |
| JP | 2019 149978 | * | 3/2018 |
| TW | 201808318 | | 3/2018 |

OTHER PUBLICATIONS

Wu, M. et al. Effects of Antrodia camphorata on Alcohol Clearance and Antifibrosis in Livers of Rats Continuously Fed Alcohol. J of Agricultural and Food Chemistry 59(8)4248-4254 Apr. 27, 2011. (Year: 2011).*

Kumar K. et al. Antioxidant Properties of Antrodia cinnamomea . . . Medicinal Plants and Fungi: Recent Advances in Research and Development Chapter 6, pp. 135-164, Springer 2017. (Year: 2017).*

Li Junpeng Et al.,Protective Effect of Taiwanofungus camphoratus Capsules on Rat Liver Injury Induced by Tetrachloromethane,China Pharmacist 2013,vol. 16,No. 7.

Liu Dianmo Et al.,Experimental study on the liver protection effect of Taiwan specialty Antrodia cinnamomea dripping pills,Chinese journal of ethnomedicine and ethnopharmacy.

Huang Gui-dong Et al.,Study on the Antialcoholism Effects of Antrodia camphorata Oral Liquid,Modem Food Science and Technology 2018, vol. 34, No. 7,China.

Lu Zhenming, Antioxidant activity and its protective effect on ethanol-induced acute liver injury in rats of the dry matter of culture broth of Antrodia camphorata,Master's Thesis of Jiangnan University,China.

* cited by examiner

*Primary Examiner* — Qiuwen Mi

(74) *Attorney, Agent, or Firm* — Muncy, Geissler, Olds & Lowe, P.C.

(57) ABSTRACT

The invention provides a usage of a *Antrodia cinnamomea* powder for preparation of a composition for dispelling the effects of alcohol, which means that by administering an effective amount of the *Antrodia cinnamomea* powder disclosed in the invention to an subject, is capable of accelerating metabolism of alcohol and/or acetaldehyde in the subject's body, reducing a content of alcohol and/or acetaldehyde in blood, and shortening the time of the subject generating intoxicated reaction in order to achieve an efficacy of dispelling the effects of alcohol.

3 Claims, 5 Drawing Sheets

USE OF ANTRODIA CINNAMOMEA FOR INCREASING ALCOHOL METABOLISM

BACKGROUND OF THE INVENTION

Field of Invention

The invention relates to a second use of *Antrodia cinnamomea*, and more particularly to a use of *Antrodia cinnamomea* for increasing alcohol metabolism or/and hangover.

Related Art

*Taiwanofungus camphoratus*, with a commonly name of *Antrodia cinnamomea*, also known as *Antrodia camphoratus*, cinnamomum fungus, fungus grown in a cavity, and godsent fungus, is a medicinal fungus belonging to the Fomitopsidaceae *Antrodia*, and only native to Taiwan. The medicinal physiological activity of *Antrodia cinnamomea* is very extensive and significant. At least 78 species have been isolated and identified, of which 39 are triterpenes, and 31 of which have confirmed their chemical structures. The chemical compounds contained in *Antrodia cinnamomea* can be roughly classified into polysaccharides, triterpenes and sterols, benzenoids, benzoquinone derivatives, maleic acid and succinic acid derivatives; and according to research, *Antrodia cinnamomea* has a variety of efficacies on subject health promotion, such as antibacterial, antiviral, antineoplastic, and enhancing organism immunity.

In addition to drinking alcohol as one of the ways for modem people to relieve stress, it is also a culture in social life. Generally speaking, moderate intake of alcohol can relax people's mind, but intaking excessive alcohol will cause discomfort such as dizziness, vomiting, low cognitive ability, nausea, and low mobility, and it may continue to affect the life of the next day. In the long run, it will also have adverse effects on health. At present, there are many products on the market that claim to have an efficacy of dispelling the effects of alcohol, for example, by intaking fructose to increase alcohol metabolism. However, using fructose to increase alcohol metabolic rate will not only increase the content of uric acid and lactic acid, but also increase the risk of suffering from metabolic syndrome.

SUMMARY OF THE INVENTION

A main object of the invention is to provide a secondary use of *Antrodia cinnamomea*, which is capable of reducing a content of alcohol and/or acetaldehyde in blood, promoting alcohol metabolism, and achieving efficacies of dispelling the effects of alcohol preventively and therapeutically.

Another object of the invention is to provide a use of *Antrodia cinnamomea* for dispelling the effects of alcohol and/or increasing alcohol metabolism, which is not hepatotoxic and is capable of improving the dehydrogenase, acetaldehyde dehydrogenase or/and SOD enzyme activity, in order to achieve efficacies of increasing alcohol metabolism, lowering alcohol concentration in the blood and treating or preventing acute alcoholism or other liver disease caused by an elevated alcohol concentration in blood.

In order to achieve the above-mentioned objects, this invention disclosed a method for enhancing the metabolism of alcohol in a subject comprising administering an effective amount of *Antrodia cinnamomea* powder or composition thereof to a subject in need of enhancing the metabolism of alcohol. It means that by administering an effective amount of the *Antrodia cinnamomea* powder to the subject who is in a need of dispelling the effects of alcohol can accelerating metabolism of alcohol and/or acetaldehyde, so that it can prevent or reduce the effects of alcohol or uncomfortable feeling from hangover efficiently.

Furthermore, in one embodiment, the invention disclosed a method for lowering the ethanol concentration in blood of a subject comprising administering an effective amount of *Antrodia cinnamomea* powder or composition thereof to a subject in need of reducing an adverse effect caused by an elevated alcohol concentration in blood, whereby the administration of *Antrodia cinnamomea* powder or composition thereof for lowering the ethanol concentration in blood.

According to the *Antrodia cinnamomea* powder or composition thereof has dual efficacies of dispelling the effects of alcohol preventively and therapeutically, which means that when the subject takes the composition for dispelling the effects of alcohol before drinking alcohol, the composition for dispelling the effects of alcohol has an efficacy of dispelling the effects of alcohol preventively; and when the subject takes the composition for dispelling the effects of alcohol after drinking alcohol, the composition for dispelling the effects of alcohol exerts an efficacy of dispelling the effects of alcohol therapeutically.

In the other embodiment, the invention disclosed the method for treating or preventing acute alcoholism or liver disease caused by an elevated plasma alcohol level in a subject comprising administering an effective amount of *Antrodia cinnamomea* powder or composition thereof to a subject who has an elevated plasma alcohol level, whereby the administration of *Antrodia cinnamomea* powder or composition thereof for increasing alcohol dehydrogenase, acetaldehyde dehydrogenase or SOD enzyme activity.

For example, when an subject intakes excessive alcohol and has symptoms of acute alcoholism, by administering an effective amount of the *Antrodia cinnamomea* powder disclosed in the invention is capable of metabolizing the alcohol in the subject's body in a short time.

In other words, the *Antrodia cinnamomea* powder can be used to prepare an alcohol metabolism accelerant or an SOD enzyme activity accelerant. And if the *Antrodia cinnamomea* powder is prepared to be the alcohol metabolism accelerant, it is capable of achieving efficacies of promoting alcohol metabolism and avoiding accumulation in the body by enhancing an activity of alcohol dehydrogenase and/or acetaldehyde dehydrogenase in the body; and if *Antrodia cinnamomea* powder is prepared to be SOD enzyme activity accelerant, when an subject takes an effective amount of the *Antrodia cinnamomea* powder after being intoxicated, an SOD enzyme activity in the body will be increased, which is not only capable of achieving an efficacy of promoting decomposition of alcohol, but also reducing an oxidative stress at the same time, in order to achieve an efficacy of protecting cells.

In the embodiments, the *Antrodia cinnamomea* powder can be made to a composition, such as a pharmaceutical preparation, a beverage, or a food product. Furthermore, the composition can be an oral or parenteral solution, a syrup, a powder, a capsule, a tablet, a beverage, a food product, or a food supplement.

In another embodiment, the effective amount of the *Antrodia cinnamomea* powder is at least 79.5 mg/day for an adult.

In the embodiments, the *Antrodia cinnamomea* powder is produced by crushing and grinding the *Antrodia cinnamomea* mycelium; for example, the *Antrodia cinnamomea* powder is made according to following steps of:

a. acquiring a *Antrodia cinnamomea* mycelium powder;

b. mixing the *Antrodia cinnamomea* mycelium powder with a grease in a predetermined weight ratio to form a *Antrodia cinnamomea* oil-phase mycelium powder;

c. preparing an aqueous-phase solution containing a water and a solute, the solute is selected from a group consisting of water-soluble salts, sugars, sugar esters and colloids, for example, the aqueous-phase solution is composed of water, sucrose fatty acid esters and dextrin fibers;

d. performing a microemulsification procedure on a *Antrodia cinnamomea* oil-phase solution and the aqueous-phase solution to obtain a *Antrodia cinnamomea* microemulsified product; and e. freezing and drying the *Antrodia cinnamomea* micro-emulsified product to obtain a water-soluble *Antrodia cinnamomea* powder.

BRIEF DESCRIPTION OF THE DRAWINGS

The objects, features, and achieved efficacies of the invention can be understood from the description, drawings and tables of the following preferred embodiments, in which.

DETAILED DESCRIPTION OF THE INVENTION

Figure 1:
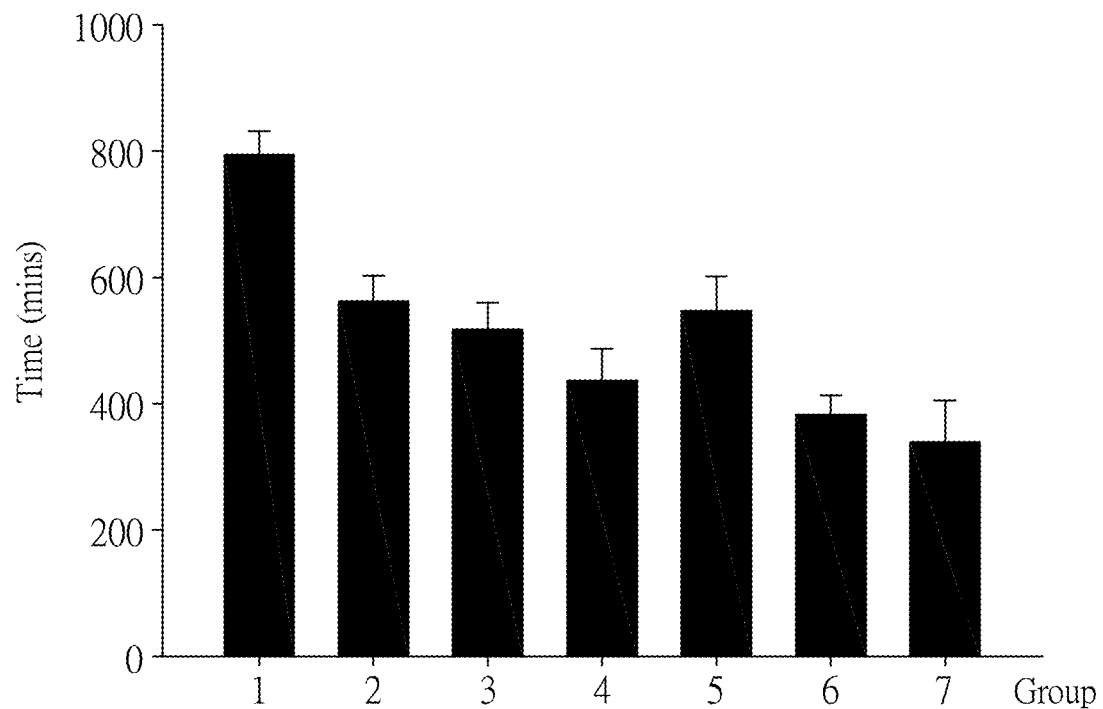
FIG. 1 shows average intoxication time of mice in each group in a first test of dispelling the effects of alcohol.

Intoxication rates of mice described in the following examples are based on whether the mice have lost righting reflex as the standard. Detection steps are as follows: after the mice are fed with alcohol, put them into a cage with their backs facing downward, if the mice keep a posture with their backs facing downward for more than 30 seconds, it is judged that the mice have lost their righting reflex and are intoxicated.

Example 1: Sample Preparation

Sample 1: water-soluble *Antrodia cinnamomea* powder, wherein the water-soluble *Antrodia cinnamomea* powder is a powdery extract obtained by supercritical carbon dioxide extraction, emulsification and drying of *Antrodia cinnamomea* mycelium powder, and after testing, it is confirmed that it contains the same content of triterpenoids as wild *Antrodia cinnamomea*.

For example, the *Antrodia cinnamomea* mycelium powder is processed with supercritical carbon dioxide extraction and then concentrated to obtain a paste-like supercritical *Antrodia cinnamomea* mycelium extract, the paste-like supercritical *Antrodia cinnamomea* mycelium extract is mixed with grease substances in a weight ratio of approximately 1:6-7 at a temperature of 70° C. to obtain a *Antrodia cinnamomea* oil-phase solution. An aqueous-phase solution is prepared, which contains water, dextrin fibers and sucrose fatty acid esters, and is mixed in a weight ratio of approximately 357-358:72:1. After the *Antrodia cinnamomea* oil-phase solution and the aqueous-phase solution are processed with a microemulsification procedure, freeze-dried and sieved to obtain a water-soluble *Antrodia cinnamomea* powder.

Sample 2: Commercially available *Hovenia dulcis* functional drink, containing 1.3% of *Hovenia dulcis* extract concentrate.

Sample 3: Commercially available patented *Hovenia dulcis* extract (Korea Lifetree Biotech Co., Ltd.).

Example 2: Preliminary Test

Three groups of mice, with 8 mice in each of the groups, are intragastrically administered with doses of 0.3 mL/20 g, 0.35 mL/20 g, and 0.4 mL/20 g of alcohol solution (58% Kinmen Kaoliang Liquor-sorghum) respectively, in order to observe an amount of alcohol required to cause lost of righting reflex (LOR) in the mice in each of the groups and none of the mice die.

It is found that a few of the mice die when 0.4 mL/20 g of alcohol solution is administered; none of the mice die when 0.35 mL/20 g of alcohol solution is administered, intoxication rate is 100%, and an average intoxication time is 794.0±38.02 minutes; none of the mice die when 0.3 mL/20 g of alcohol solution is administered, and intoxication rate is 25%; therefore, the mice are intragastrically administered with 0.35 mL/20 g of alcohol solution in the subsequent tests of dispelling the effects of alcohol.

Example 3: Test (1) of Dispelling the Effects of Alcohol

The mice are randomly divided into groups, wherein:

the first group is a blank group, and is administered with an equal volume of physiological saline;

the second group is a water-soluble *Antrodia cinnamomea* powder low-dose group, and is administered with a dose of 16.3 mg/kg;

the third group is a water-soluble *Antrodia cinnamomea* powder medium-dose group, and is administered with a dose of 32.8 mg/kg;

the fourth group is a water-soluble *Antrodia cinnamomea* powder high-dose group, and is administered with a dose of 49.2 mg/kg;

the fifth group is a *Hovenia dulcis* functional drink group, and is administered with a dose of 3.38 g/kg;

the sixth group of a patented *Hovenia dulcis* extract group, and is administered with a dose of 504.3 mg/kg; and the seventh group is a mixed group, which is administered with *Hovenia dulcis* functional drink (dose 3.38 g/kg) and water-soluble *Antrodia cinnamomea* powder (dose 16.3 mg/kg) at the same time.

The mice in each of the groups are fasted for 12 hours, and then are treated according to the above-mentioned conditions in each of the groups. After 30 minutes, all the mice in each of the groups except the first group are intragastrically administered with 0.35 mL/20 g of 58% Kinmen Kaoliang Liquor by body weight, intoxication time (meaning the time from being conscious to lost of righting reflex) of the mice in each of the groups is observed and recorded in order to calculate and obtain intoxication rates within 24 hours, wherein whether the mice are intoxicated or not is based on whether the mice have lost righting reflex as the standard.

It is found that the intoxication rates of the mice in each of the groups are 100%, and none of the mice die. From the results in FIG. 1, it can be known that an average intoxication time of the mice in the first group is 794.0±38.02 minutes; average intoxication time of the mice in the second group to the fourth group is 562.5±38.03 minutes, 517±41.16 minutes and 437.5±49.27 minutes respectively; an average intoxication time of the mice in the fifth group is 546.38±53.42 minutes; an average intoxication time of the mice in the sixth group is 382.5±29.58 minutes; and an average intoxication time of the mice in the seventh group is 338.37±64.18 minutes.

Although the results in FIG. 1 show that administration of the patented *Hovenia dulcis* extract has a shorter intoxication time, its dose is 504.3 mg/day; while at a low dose of 16.3 mg/day the water-soluble *Antrodia cinnamomea* powder disclosed in the invention already produces an effect of dispelling the effects of alcohol (compared to the first group); and comparing the administered dose of the sixth group with that of the second group, it can be known that when an administered dose of the water-soluble *Antrodia cinnamomea* powder disclosed in the invention is only 1/30 times of that of the patented *Hovenia dulcis* extract, the water-soluble *Antrodia cinnamomea* powder is already capable of achieving an effect of dispelling the effects of alcohol, which means that the water-soluble *Antrodia cinnamomea* powder disclosed in the invention is capable of achieving an effect of dispelling the effects of alcohol significantly better than the prior art. If the water-soluble *Antrodia cinnamomea* powder is to be applied to the human body, calculated according to conversion standard of administered doses of human and mice, for adults of 60 kg, 2460 mg/day of patented *Hovenia dulcis* extract must be administered to achieve an efficacy of dispelling the effects of alcohol preventively, while administration of only 79.5 mg/day of the water-soluble *Antrodia cinnamomea* powder disclosed in the invention is already capable of achieving an efficacy of dispelling the effects of alcohol preventively. It can be known from the above results that an efficacy of dispelling the effects of alcohol preventively can be effectively achieved by administering the water-soluble *Antrodia cinnamomea* powder disclosed in the invention, and an effect of dispelling the effects of alcohol preventively is improved with increasing dose; and after mixing the water-soluble *Antrodia cinnamomea* powder disclosed in the invention with the commercially available *Hovenia dulcis* functional drink, an effect of dispelling the effects of alcohol preventively can be improved substantially.

Example 4: Test (2) of Dispelling the Effects of Alcohol

The mice in each of the groups are fasted for 12 hours as described in Example 3, and all the mice are intragastrically administered with 0.35 mL/20 g of 58% Kinmen Kaoliang Liquor by body weight. After 30 minutes, the first group is administered with an equal volume of physiological saline, the mice in the second group to the seventh group are administered in a one-time administration; then sober time (meaning the time from lost of righting reflex to being conscious) of the mice in each of the groups is observed, and 0, 60, 120, 240 and 360 minutes after being fed with alcohol, blood is collected to determine contents of alcohol and acetaldehyde in the blood, the results are shown in FIG. 2 to FIG. 4, Table 1 and Table 2.

In this experiment, alcohol solution (0.35 mL/20 g) is administered first, and then drug is administered. Intoxication rates of each of the groups are 100%, and none of the mice die. From the results in FIG. 2, it can be known that an average intoxication time of the mice in the first group is 740.5±30.59 minutes; average intoxication time of the mice in the second group to the fourth group is 541.37±40.63 minutes, 494.25±46.29 minutes and 438±18.96 minutes respectively; an average intoxication time of the mice in the fifth group is 495.38±56.37 minutes; an average intoxication time of the mice in the sixth group is 366.5±44.78 minutes; and an average intoxication time of the mice in the seventh group is 322.63±53.51 minutes. The results show that the water-soluble *Antrodia cinnamomea* powder disclosed in the invention does have an effect of dispelling the effects of alcohol therapeutically, and as described in the foregoing examples, the water-soluble *Antrodia cinnamomea* powder disclosed in the invention is capable of achieving an efficacy of dispelling the effects of alcohol under low-dose condition.

Figure 2:
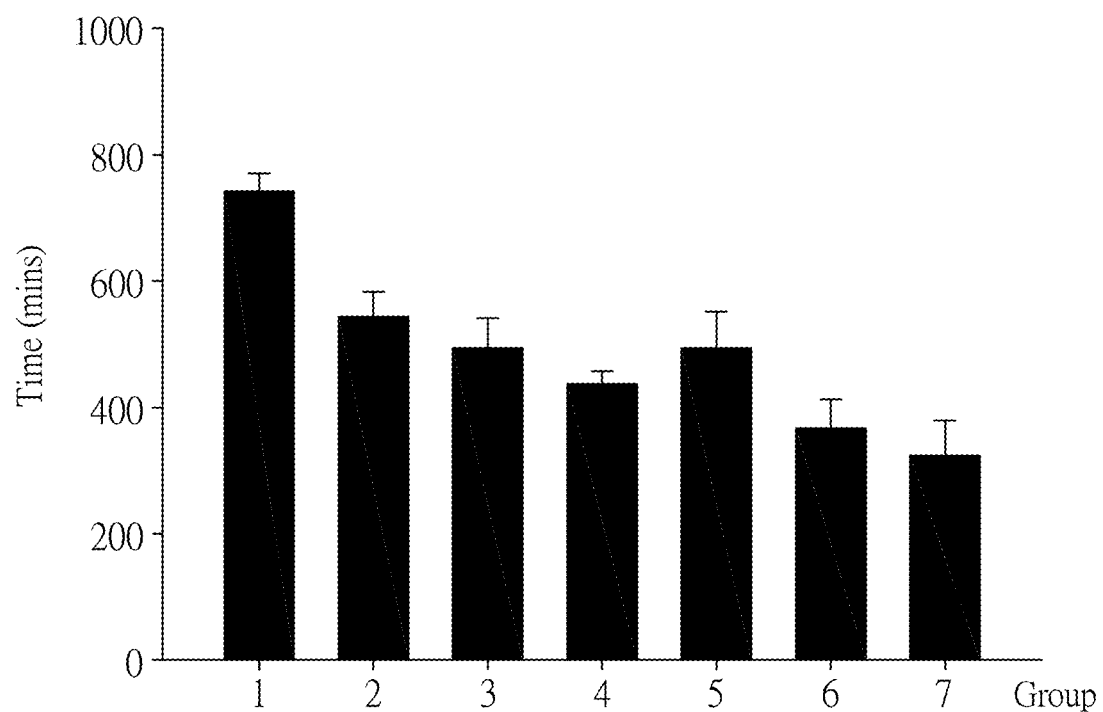
FIG. 2 shows average intoxication time of the mice in each of the groups in a second test of dispelling the effects of alcohol.
Figure 3:
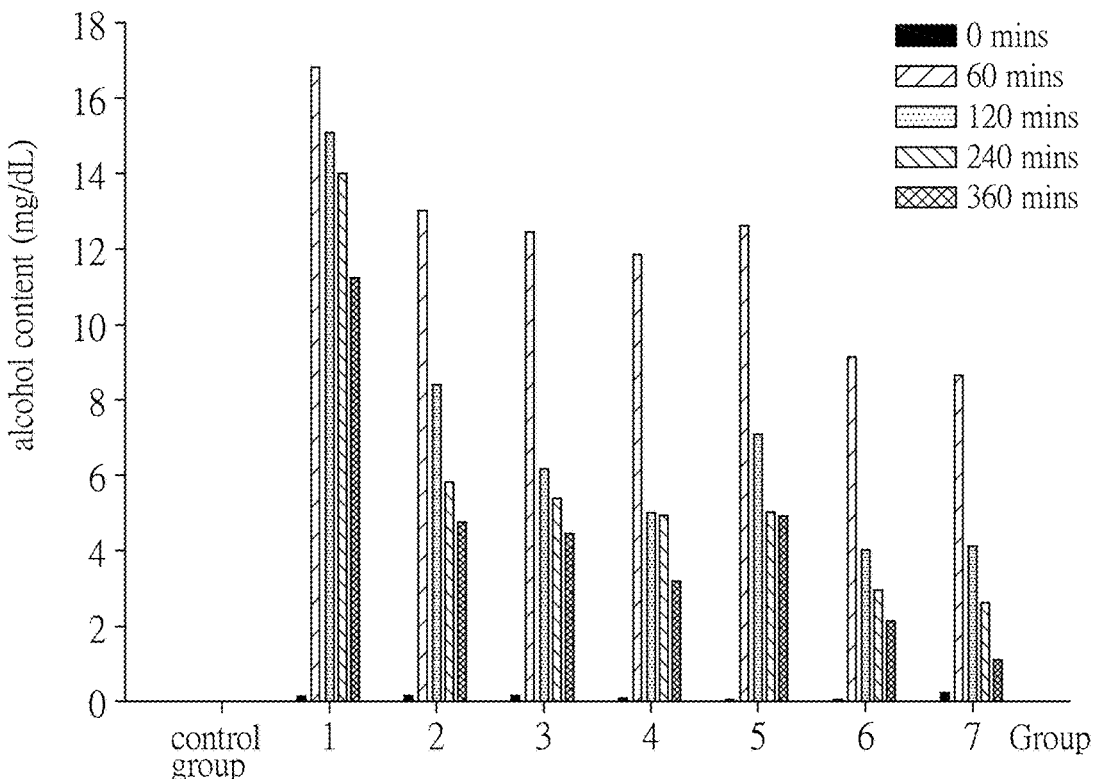
FIG. 3 shows alcohol contents in the blood of the mice in each of the groups in the second test of dispelling the effects of alcohol.
Figure 4:
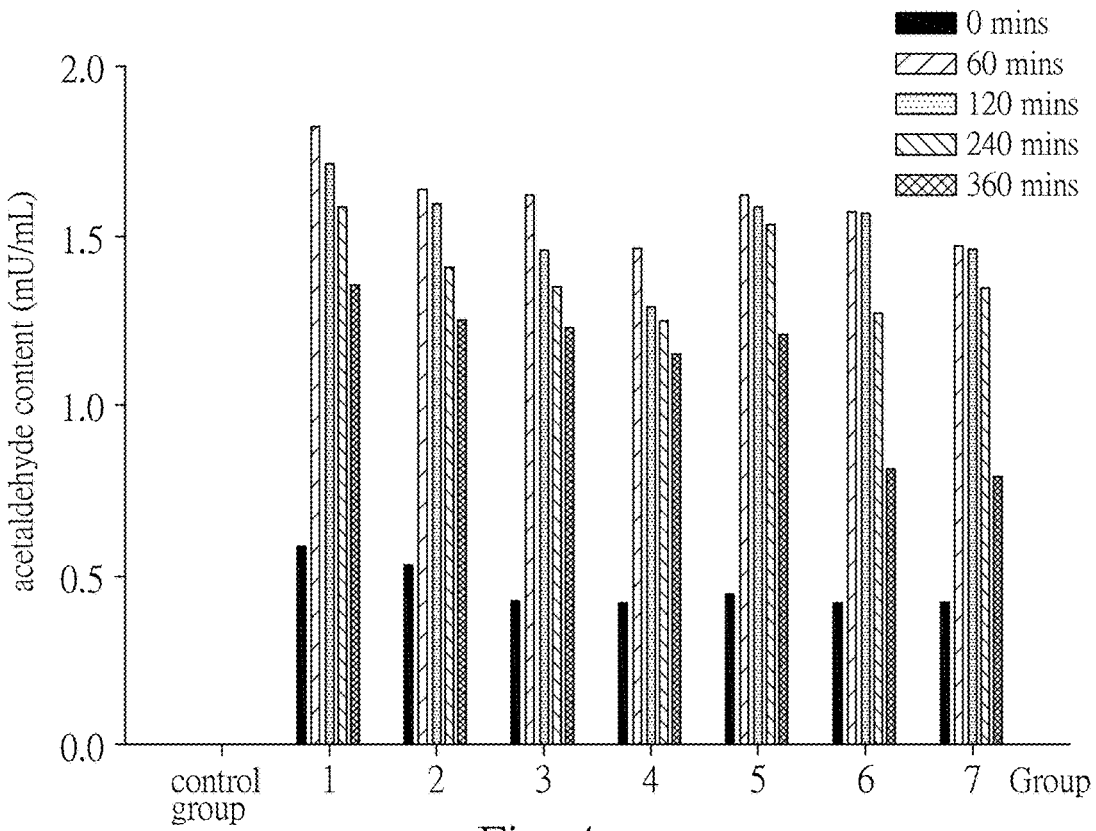
FIG. 4 shows acetaldehyde contents in the blood of the mice in each of the groups in the second test of dispelling the effects of alcohol.

From the results in FIG. 2 to FIG. 4, Table 1 and Table 2, it can be known that alcohol and acetaldehyde contents of the mice in the alcohol group that are only administered with alcohol solution orally are 1.48±0.02 mg/dL and 8.09±0.98 mU/mL respectively at 120 minutes, there is a significant increase; and from the results of the second group to the fourth group, it can be known that the second group to the fourth group that are administered with the water-soluble *Antrodia cinnamomea* powder disclosed in the invention after being administered with alcohol orally, alcohol and acetaldehyde contents measured in the blood of the mice respectively show a downward trend at 120 minutes. Specifically, alcohol and acetaldehyde contents measured in the blood of the mice in the second group at 120 minutes are 1.07±0.05 mg/dL and 6.59±0.57 mU/mL respectively; alcohol and acetaldehyde contents measured in the blood of the mice in the third group at 120 minutes are 1.03±0.03 mg/dL and 6.24±1.02 mU/mL respectively; and alcohol and acetaldehyde contents measured in the blood of the mice in the fourth group at 120 minutes are 0.80±0.03 mg/dL and 5.73±1.01 mU/mL respectively. 120 minutes after being fed with alcohol, alcohol and acetaldehyde contents measured in the blood of the mice in the fifth group are 1.19±0.03 mg/dL and 6.91±0.89 mU/mL respectively; alcohol and acetaldehyde contents measured in the blood of the mice in the sixth group are 0.70±0.04 mg/dL and 5.34±1.49 mU/mL respectively; and alcohol and acetaldehyde contents measured in the blood of the mice in the seventh group are 0.62±0.04 mg/dL and 4.64±0.84 mU/mL respectively.

It can be known from the above results that the mice disclosed in this example are indeed acute alcoholic mice after being fed with alcohol, and administration of the water-soluble *Antrodia cinnamomea* powder disclosed in the invention is capable of effectively increasing an efficiency of dispelling the effects of alcohol and shortening the time required for the mice to be sobered from alcohol, and as an administered dose increases, the time required for dispelling the effects of alcohol is shortened; blood test results more clearly confirm that the water-soluble *Antrodia cinnamomea* powder disclosed in the invention is capable of metabolizing alcohol and acetaldehyde in blood, and reducing alcohol and acetaldehyde contents in blood.

TABLE 1 alcohol content (mg/dL) in the blood of the mice (acute alcoholic mice) in each of the groups at different times after different treatments

| Group | Time after feeding with alcohol (minutes) | | | | |
|---|---|---|---|---|---|
| | 0 | 60 | 120 | 240 | 360 |
| | Alcohol content in blood (mg/dL) | | | | |
| First group | 0.00 ± 0.00 | 0.00 ± 0.00 | 0.00 ± 0.00 | 0.00 ± 0.00 | 0.00 ± 0.00 |
| Alcohol group | 0.01 ± 0.01 | 1.17 ± 0.03 | 1.48 ± 0.02 | 1.24 ± 0.10 | 1.06 ± 0.03 |
| Second group | 0.02 ± 0.02 | 0.58 ± 0.03 | 1.07 ± 0.05 | 0.85 ± 0.03 | 0.44 ± 0.03 |
| Third group | 0.01 ± 0.01 | 0.53 ± 0.03 | 1.03 ± 0.03 | 0.74 ± 0.02 | 0.37 ± 0.02 |
| Fourth group | 0.01 ± 0.01 | 0.51 ± 0.07 | 0.80 ± 0.03 | 0.49 ± 0.01 | 0.27 ± 0.02 |
| Fifth group | 0.01 ± 0.02 | 0.66 ± 0.03 | 1.19 ± 0.03 | 0.95 ± 0.07 | 0.65 ± 0.03 |
| Sixth group | 0.01 ± 0.01 | 0.46 ± 0.04 | 0.70 ± 0.04 | 0.39 ± 0.02 | 0.21 ± 0.03 |
| Seventh group | 0.01 ± 0.01 | 0.41 ± 0.02 | 0.62 ± 0.04 | 0.31 ± 0.02 | 0.16 ± 0.02 |

TABLE 2 acetaldehyde content (mg/dL) in the blood of the mice (acute alcoholic mice) in each of the groups at different times after different treatments

| Group | Time after feeding with alcohol (minutes) | | | | |
|---|---|---|---|---|---|
| | 0 | 60 | 120 | 240 | 360 |
| | Acetaldehyde content in blood (mg/dL) | | | | |
| First group | 0.00 ± 0.00 | 0.00 ± 0.00 | 0.00 ± 0.00 | 0.00 ± 0.00 | 0.00 ± 0.00 |
| Alcohol group | 0.36 ± 0.15 | 3.57 ± 0.77 | 8.09 ± 0.98 | 6.78 ± 0.53 | 5.51 ± 0.41 |
| Second group | 0.33 ± 0.18 | 3.16 ± 0.54 | 6.59 ± 0.57 | 5.76 ± 1.50 | 3.78 ± 1.22 |
| Third group | 0.41 ± 0.24 | 2.94 ± 0.94 | 6.24 ± 1.02 | 5.49 ± 0.71 | 3.54 ± 0.78 |
| Fourth group | 0.37 ± 0.26 | 2.70 ± 0.79 | 5.73 ± 1.01 | 4.87 ± 1.52 | 3.31 ± 0.41 |
| Fifth group | 0.51 ± 0.26 | 3.36 ± 1.75 | 6.91 ± 0.89 | 6.01 ± 1.02 | 4.04 ± 0.80 |
| Sixth group | 0.60 ± 0.28 | 2.37 ± 0.49 | 5.34 ± 1.49 | 4.45 ± 1.74 | 3.08 ± 0.87 |
| Seventh group | 0.34 ± 0.27 | 2.23 ± 1.04 | 4.64 ± 0.84 | 3.65 ± 0.37 | 2.70 ± 0.94 |

Example 5: Test (3) of Dispelling the Effects of Alcohol

A test method of this example is basically the same as that of example 3, except that the mice are randomly divided into four groups, each of the groups with 10 mice, wherein;

the first group is a normal group, and is administered with an equal volume of physiological saline;

the second group is a *Antrodia cinnamomea* mycelium powder low-dose group, and is administered with a dose of 82.5 mg/kg;

the third group is a *Antrodia cinnamomea* mycelium powder high-dose group, and is administered with a dose of 165 mg/kg; and the fourth group is a silymarin group.

Wherein the *Antrodia cinnamomea* mycelium powder is obtained by grinding *Antrodia cinnamomea* mycelium.

Except for the first group, the mice in each of the groups are intragastrically administered with 0.35 mL/20 g of 58% Kinmen Kaoliang Liquor by body weight, and intoxication time (meaning the time from being conscious to lost of righting reflex) of the mice in each of the groups is observed and recorded in order to calculate and obtain intoxication rates within 24 hours.

It can be known from the results that intoxication rates of the mice in each of the groups are 100%, and none of the mice die; an average intoxication time of the mice in the first group is 853.67±9.61 minutes; average intoxication time of the mice in the second group and the third group is 638.38±37.42 minutes and 458.25±55.89 minutes respectively; and an average intoxication time of the mice in the fourth group is 453.75±34.19 minutes.

The above results show that the *Antrodia cinnamomea* mycelium powder disclosed in the invention does have an efficacy of dispelling the effects of alcohol preventively, and when it reaches twice the dose, its efficacy of dispelling the effects of alcohol preventively is similar to that of the drug silymarin.

Example 6: Test (4) of Dispelling the Effects of Alcohol

A test method of this example is basically the same as that of example 4, and grouping of the mice and their treatment conditions are the same as those described in example 5. 30 minutes after alcohol solution is administered, the mice are administered in a one-time administration separately. Time required for being sobered is recorded, and blood is collected at 0, 60, 120, 240 and 360 minutes after alcohol is fed to determine alcohol and acetaldehyde contents in the blood, the results are shown in Table 3 and Table 4 below.

It can be known from the experimental results that an average intoxication time of the mice in the first group is 745.83±18.17 minutes; average intoxication time of the mice in the second group and the third group is 547.13±32.35 minutes and 340.63±34.45 minutes respectively; and an average intoxication time of the mice in the fourth group is 328.38±35.52 minutes.

It can be known that administration of the *Antrodia cinnamomea* mycelium powder disclosed in the invention after being fed with alcohol is capable of reducing the intoxication time, which shows that the *Antrodia cinnamomea* mycelium powder disclosed in the invention does have an efficacy of dispelling the effects of alcohol therapeutically; and from the results in Table 3 and Table 4, it can be known that the *Antrodia cinnamomea* mycelium powder disclosed in the invention is capable of reducing alcohol and acetaldehyde contents in blood, wherein when twice the dose is administered, an efficacy of the *Antrodia cinnamomea* mycelium powder disclosed in the invention of reducing alcohol and acetaldehyde contents in blood is better than that of administration of the drug silymarin.

TABLE 3 alcohol content (mg/dL) in the blood of the mice (acute alcoholic mice) in each of the groups at different times after different treatments

| | Time after feeding with alcohol (minutes) | | | | |
|---|---|---|---|---|---|
| | 0 | 60 | 120 | 240 | 360 |
| Group | Alcohol content in blood (mg/dL) | | | | |
| First group | 0.00 ± 0.00 | 0.00 ± 0.00 | 0.00 ± 0.00 | 0.00 ± 0.00 | 0.00 ± 0.00 |
| Alcohol group | 0.01 ± 0.00 | 0.94 ± 0.03 | 1.20 ± 0.06 | 1.07 ± 0.00 | 0.87 ± 0.04 |
| Second group | 0.02 ± 0.05 | 0.8 ± 0.01 | 1.01 ± 0.03 | 0.94 ± 0.04 | 0.75 ± 0.03 |
| Third group | 0.00 ± 0.01 | 0.41 ± 0.03 | 0.7 ± 0.06 | 0.72 ± 0.05 | 0.41 ± 0.04 |
| Fourth group | 0.00 ± 0.01 | 0.63 ± 0.07 | 0.91 ± 0.04 | 0.84 ± 0.04 | 0.58 ± 0.03 |

TABLE 4 acetaldehyde content (mg/dL) in the blood of the mice (acute alcoholic mice) in each of the groups at different times after different treatments

| | Time after feeding with alcohol (minutes) | | | | |
|---|---|---|---|---|---|
| | 0 | 60 | 120 | 240 | 360 |
| Group | Acetaldehyde content in blood (mg/dL) | | | | |
| First group | 0.00 ± 0.00 | 0.00 ± 0.00 | 0.00 ± 0.00 | 0.00 ± 0.00 | 0.00 ± 0.00 |
| Alcohol group | 0.42 ± 0.86 | 4.12 ± 0.77 | 6.55 ± 1.11 | 5.59 ± 0.86 | 4.81 ± 0.28 |
| Second group | 0.34 ± 0.21 | 3.55 ± 0.64 | 5.68 ± 0.27 | 5.29 ± 0.73 | 4.55 ± 1.01 |
| Third group | 0.44 ± 0.23 | 2.72 ± 0.73 | 4.24 ± 0.98 | 3.72 ± 0.13 | 2.92 ± 1.19 |
| Fourth group | 0.38 ± 0.56 | 3.10 ± 0.73 | 4.71 ± 0.53 | 4.57 ± 0.21 | 3.58 ± 0.48 |

Example 7: Alcohol Metabolism Test

The mice are randomly divided into four groups, 12 in each of the groups, wherein:

a *Antrodia cinnamomea* low-dose group: 1 ml of water is mixed with 1 fold of dose (82.5 mg/kg) of the *Antrodia cinnamomea* mycelium powder daily;

a *Antrodia cinnamomea* high-dose group: 1 ml of water is mixed with 2 fold of dose (165 mg/kg) of the *Antrodia cinnamomea* mycelium powder daily;

a silymarin group: a silymarin dose of 40 mg/kg; and a normal group and an alcohol group: 1 ml of water respectively.

Figure 5:
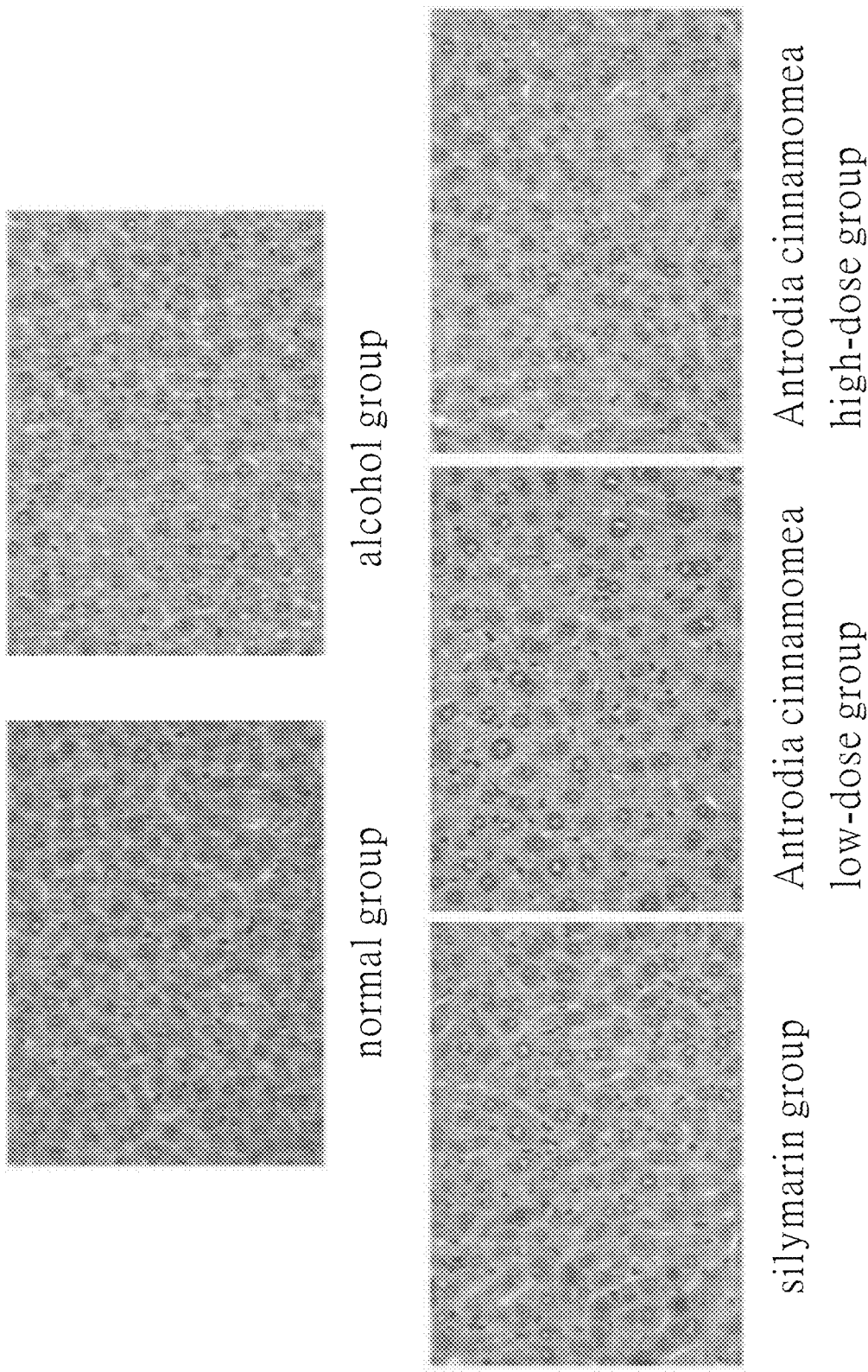
FIG. 5 is staining diagrams of liver section tissues of the mice in each of the groups in an alcohol metabolism test.

After the mice in each of the groups are treated with the above conditions for 4 weeks, except for the normal group, each of the groups is administered with 0.35 ml of alcohol/mouse (10 ml/kg+50% alcohol volume daily converted based on surface areas of human body and mouse body), the alcohol group is administered with 0.35 ml of water/mouse half an hour after being fed with alcohol, and the *Antrodia cinnamomea* high-dose group and the *Antrodia cinnamomea* low-dose group are respectively administered with 0.35 ml of the *Antrodia cinnamomea* mycelium powder/mouse half an hour after being fed with alcohol. After the experiments are done, liver form and conditions, body weight, and liver index of the mice in each of the groups are observed, as shown in Table 5 and FIG. 5.

Serum and liver biochemical values of the mice in each of the groups are tested, and the results are shown in Table 6. From the results in Table 6, it can be known that triglycerides, GOT and GPT of the mice in the alcohol group have increased, and administration of the *Antrodia cinnamomea* mycelium powder disclosed in the invention is capable of reducing triglycerides, GOT and GPT, and an effect of high dose is better, even better than an effect of the drug silymarin. Furthermore, alcohol dehydrogenase and acetaldehyde dehydrogenase activities of the mice in the alcohol group have decreased, and administration of the *Antrodia cinnamomea* mycelium powder disclosed in the invention is capable of increasing the activities of alcohol dehydrogenase and acetaldehyde dehydrogenase, but administration of silymarin does not have an efficacy of increasing the activities of alcohol dehydrogenase and acetaldehyde dehydrogenase.

From the results in Table 7 and Table 8, it can be known that alcohol and acetaldehyde contents of the mice in the alcohol group are 1.15±0.01 mg/dL and 6.80±0.37 mU/mL respectively when being fed with alcohol solution at 120 minutes, which have increased in comparing with the mice in the normal group, but after continuously taking the *Antrodia cinnamomea* powder disclosed in the invention for 30 days, both the alcohol and acetaldehyde contents decrease. At 120 minutes, alcohol contents of the *Antrodia cinnamomea* powder low-dose group and the *Antrodia cinnamomea* mycelium powder high-dose group are 1.03±0.03 mg/dL and 0.81±0.04 mg/dL respectively, and acetaldehyde contents of the *Antrodia cinnamomea* powder low-dose group and the *Antrodia cinnamomea* mycelium powder high-dose group are 4.45±0.6 mU/mL and 3.49±0.48 mU/mL respectively. At 360 minutes, alcohol contents of the *Antrodia cinnamomea* mycelium powder low-dose group and the *Antrodia cinnamomea* powder high-dose group are 0.58±0.03 mg/dL and 0.37±0.05 mg/dL respectively, and acetaldehyde contents of the *Antrodia cinnamomea* mycelium powder low-dose group and the *Antrodia cinnamomea* powder high-dose group are 3.30±0.30 mU/mL and 2.30±0.83 mU/mL respectively; the above results show that the *Antrodia cinnamomea* mycelium powder disclosed in the invention is capable of strengthening alcohol metabolism, and with high doses, its alcohol metabolism effect is better, with an effect better than that of silymarin.

Figure 6:
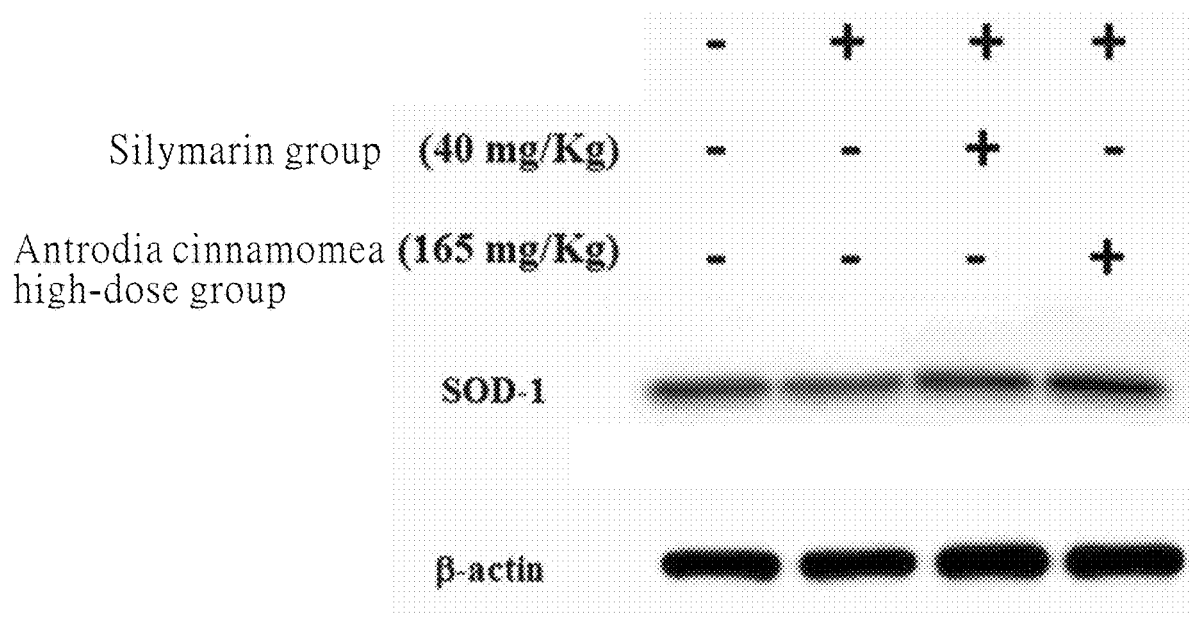
FIG. 6 shows the results of detecting SOD enzyme activity in the mice livers processed with different treatments.

Referring to FIG. 6, in terms of SOD enzyme activity, liver SOD enzyme activities of the mice fed with alcohol only have decreased, and administration of the *Antrodia cinnamomea* mycelium powder disclosed in the invention is capable of increasing the SOD enzyme activity. When twice the dose is administered, an activity of SOD enzyme in liver can be increased by 34%, which is higher than 12% of the silymarin group.

TABLE 5 body weight and liver index of the mice in each of the groups

| | Weight (g) | Liver index (%) |
|---|---|---|
| Normal group | 38.4 ± 2.08 | 5.7 ± 0.4 |
| Alcohol group | 37.91 ± 1.81 | 5.11 ± 0.4 |
| Antrodia cinnamomea mycelium powder low-dose group | 37.63 ± 1.19 | 5.39 ± 0.3 |
| Antrodia cinnamomea mycelium powder high-dose group | 37.86 ± 1.26 | 5.52 ± 0.4 |
| Silymarin group | 37.93 ± 1.12 | 5.55 ± 0.4 |

TABLE 6 results of blood test of the mice in each of the groups

| | Triglycerides | Aspartate Aminotransferase (GOT) | Alanine Aminotransferase (GPT) | Alcohol Dehydrogenase (ADH) | Acetaldehyde Dehydrogenase (ALDH) |
|---|---|---|---|---|---|
| Normal group | 99.38 ± 5.62 | 65.63 ± 6.98 | 40.38 ± 7.83 | 33.83 ± 1.49 | 33.83 ± 1.48 |
| Alcohol group | 109.37 ± 16.13 | 77.88 ± 8.35 | 54.63 ± 8.3 | 32.66 ± 0.18 | 32.22 ± 0.96 |
| Antrodia cinnamomea mycelium powder low-dose group | 92.5 ± 7.07 | 54.63 ± 4.87 | 31.13 ± 12.80 | 39.38 ± 1.46 | 41.79 ± 2.03 |
| Antrodia cinnamomea mycelium powder high-dose group | 89.37 ± 5.63 | 52.88 ± 7.61 | 29.38 ± 4.14 | 45.66 ± 2.68 | 45.66 ± 2.67 |
| Silymarin group | 93.75 ± 19.41 | 58.13 ± 13.62 | 33.88 ± 7.94 | 34.43 ± 0.99 | 34.58 ± 1.04 |

TABLE 7 alcohol content (mg/dL) in the blood of the mice in each of the groups
at different times after different treatments

| | Time after feeding with alcohol (minutes) | | | | |
|---|---|---|---|---|---|
| | 0 | 60 | 120 | 240 | 360 |
| Group | Alcohol content in blood (mg/dL) | | | | |
| Normal group | 0.00 ± 0.00 | 0.00 ± 0.00 | 0.00 ± 0.00 | 0.00 ± 0.00 | 0.00 ± 0.00 |
| Alcohol group | 0.01 ± 0.00 | 0.78 ± 0.03 | 1.15 ± 0.01 | 1.05 ± 0.03 | 0.79 ± 0.06 |
| Antrodia cinnamomea mycelium powder low-dose group | 0.00 ± 0.00 | 0.59 ± 0.03 | 1.03 ± 0.03 | 0.86 ± 0.03 | 0.58 ± 0.03 |
| Antrodia cinnamomea mycelium powder high-dose group | 0.01 ± 0.01 | 0.36 ± 0.07 | 0.81 ± 0.04 | 0.56 ± 0.06 | 0.37 ± 0.05 |
| Silymarin group | 0.01 ± 0.01 | 0.47 ± 0.05 | 0.94 ± 0.01 | 0.75 ± 0.05 | 0.52 ± 0.03 |

TABLE 8 acetaldehyde content (mg/dL) in the blood of the mice in each of the
groups at different times after different treatments

| | Time after feeding with alcohol (minutes) | | | | |
|---|---|---|---|---|---|
| | 0 | 60 | 120 | 240 | 360 |
| Group | Acetaldehyde content in blood (mg/dL) | | | | |
| Normal group | 0.00 ± 0.00 | 0.00 ± 0.00 | 0.00 ± 0.00 | 0.00 ± 0.00 | 0.00 ± 0.00 |
| Alcohol group | 0.47 ± 1.05 | 5.41 ± 0.72 | 6.80 ± 0.37 | 5.74 ± 0.36 | 4.84 ± 0.36 |
| Antrodia cinnamomea mycelium powder low-dose group | 0.39 ± 0.14 | 3.12 ± 0.18 | 4.45 ± 0.60 | 3.95 ± 0.38 | 3.30 ± 0.30 |
| Antrodia cinnamomea mycelium powder high-dose group | 0.52 ± 0.26 | 1.98 ± 0.92 | 3.49 ± 0.48 | 3.02 ± 0.66 | 2.30 ± 0.83 |
| Silymarin group | 0.41 ± 0.22 | 2.43 ± 0.47 | 4.02 ± 0.79 | 3.45 ± 0.95 | 2.83 ± 0.71 |

Example 8: Human Body Test 15 subjects are divided into three groups after taking alcoholic beverages orally. The first group does not take any products for dispelling the effects of alcohol, and the second group and the third group take the water-soluble *Antrodia cinnamomea* powder and its aqueous-phase solution disclosed in the invention, respectively, wherein a dose is 400 mg; and alcohol concentration in the breath of the subjects in each of the groups is measured at 0, 15, 30, 60, 120 and 180 minutes after being administered. The results are shown in FIG. 7.

Figure 7:
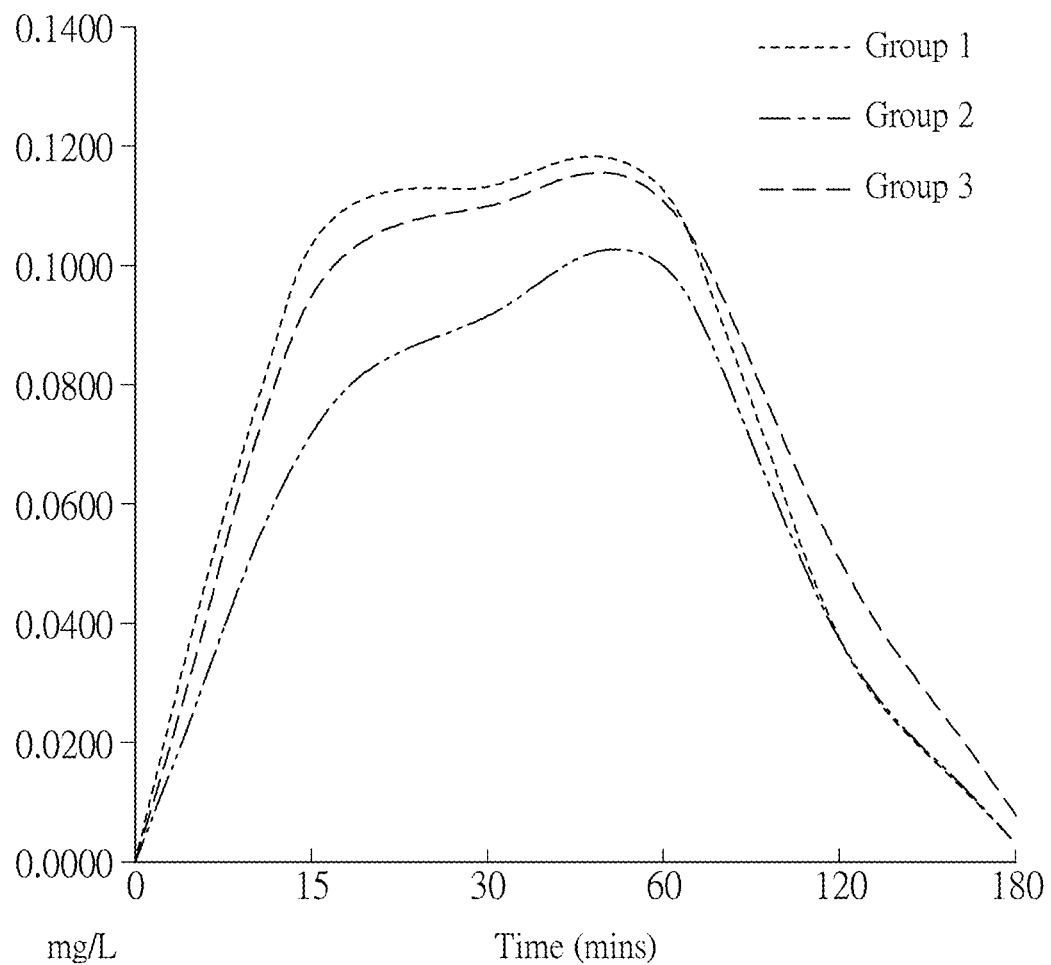
FIG. 7 shows the results of detecting alcohol concentration in the breath of subjects in each group.

It can be known from the results in FIG. 7 that taking the water-soluble *Antrodia cinnamomea* powder disclosed in the invention after drinking alcohol is capable of accelerating metabolism and decomposition of alcohol, and reducing alcohol concentration in the body. Moreover, when taking the water-soluble *Antrodia cinnamomea* powder disclosed in the invention being dissolved in water is capable of improving an efficiency of dispelling the effects of alcohol.

From the results of the above examples, it can be known that the *Antrodia cinnamomea* mycelium powder disclosed in the invention does have efficacies of enhancing alcohol metabolism and dispelling the effects of alcohol preventively, and is also capable of improving an activity of SOD enzymes in liver; and the water-soluble *Antrodia cinnamomea* powder obtained from the supercritically extracted *Antrodia cinnamomea* mycelium powder disclosed in the invention is capable of achieving the same or even better efficacies of metabolizing alcohol and dispelling the effects of alcohol preventively at a lower dose; and therefore it can be known that the *Antrodia cinnamomea* mycelium powder and its water-soluble powder disclosed in the invention can be used as effective ingredients in a medical composition for treatment or prevention of intoxication and related liver diseases.

It is to be understood that the above description is only preferred embodiments of the present invention and is not used to limit the present invention, and changes in accordance with the concepts of the present invention may be made without departing from the spirit of the present invention, for example, the equivalent effects produced by various transformations, variations, modifications and applications made to the configurations or arrangements shall still fall within the scope covered by the appended claims of the present invention.

What is claimed is:

1. A method for enhancing the metabolism of alcohol in a subject consisting of administering an effective amount of *Antrodia cinnamomea* powder to the subject in need of enhancing the metabolism of alcohol, wherein the effective amount of the *Antrodia cinnamomea* powder is at least 79.5 mg/day for an adult.

2. The method as claimed in claim 1, wherein the *Antrodia cinnamomea* powder is taken orally.

3. The method as claimed in claim 1, wherein the *Antrodia cinnamomea* powder is made according to following steps of:
   a. acquiring a *Antrodia cinnamomea* mycelium powder;
   b. mixing the *Antrodia cinnamomea* mycelium powder with a grease to form a *Antrodia cinnamomea* oil-phase solution;
   c. preparing an aqueous-phase solution containing a water and a solute, the solute is selected from a group consisting of water-soluble salt, sugar and sugar ester;
   d. performing a microemulsification procedure on the *Antrodia cinnamomea* oil-phase solution and the aqueous-phase solution to obtain a *Antrodia cinnamomea* micro-emulsified product; and
   e. freezing and drying the *Antrodia cinnamomea* micro-emulsified product to obtain the *Antrodia cinnamomea* powder which is water-soluble.

\* \* \* \* \*